(12) United States Patent
Howard

(10) Patent No.: US 8,092,715 B2
(45) Date of Patent: Jan. 10, 2012

(54) FORMULATIONS AND METHOD FOR RAISING THE FLASH POINTS OF VOLATILE ORGANIC SOLVENTS

(75) Inventor: Harry W. Howard, Little Egg Harbor, NJ (US)

(73) Assignee: GreenSolve, LLC, Binghamton, NY (US)

( * ) Notice: Subject to any disclaimer, the term of this patent is extended or adjusted under 35 U.S.C. 154(b) by 16 days.

(21) Appl. No.: 12/637,175

(22) Filed: Dec. 14, 2009

(65) Prior Publication Data

US 2011/0140047 A1 Jun. 16, 2011

(51) Int. Cl.
- C09K 3/00 (2006.01)
- C10L 1/182 (2006.01)
- C11D 7/50 (2006.01)

(52) U.S. Cl. ............. 252/364; 252/182.29; 44/452; 44/451; 510/407

(58) Field of Classification Search ............ 44/452, 44/451; 252/364, 182.29; 510/407, 411
See application file for complete search history.

(56) References Cited

U.S. PATENT DOCUMENTS

| | | | |
|---|---|---|---|
| 3,705,941 A * | 12/1972 | Hennart et al. | 514/136 |
| 3,867,526 A * | 2/1975 | Hennart et al. | 514/136 |
| 5,393,451 A * | 2/1995 | Koetzle | 510/365 |
| 5,405,547 A | 4/1995 | Rinehart | |
| 5,425,893 A * | 6/1995 | Stevens | 134/1 |
| 5,597,788 A * | 1/1997 | Stevens | 510/212 |
| 6,843,812 B2 * | 1/2005 | Stephanos | 44/266 |
| 6,897,008 B1 * | 5/2005 | Hendrickson et al. | 430/306 |
| 7,176,174 B2 | 2/2007 | Filippini et al. | |
| 7,273,839 B2 * | 9/2007 | Koetzle | 510/407 |
| 7,309,684 B2 | 12/2007 | Filippini et al. | |
| 7,833,959 B1 * | 11/2010 | Koetzle | 510/407 |
| 2005/0100823 A1 * | 5/2005 | Hendrickson et al. | 430/300 |
| 2006/0019332 A1 | 1/2006 | Zhang et al. | |
| 2006/0081822 A1 * | 4/2006 | Koetzle | 252/601 |
| 2008/0271761 A1 | 11/2008 | Sherrel et al. | |
| 2010/0187478 A1 * | 7/2010 | Howard | 252/364 |
| 2010/0247784 A1 * | 9/2010 | Koetzle | 427/386 |

FOREIGN PATENT DOCUMENTS

WO 2008/105758 A1 9/2008

OTHER PUBLICATIONS

"Clean Cities of Middle Tennessee"; http://web.archive.org/web/20080405060339/http://www.tennesseecleanfuels.org/Methanol.html; Apr. 5, 2008; 2 pages.

"Cargill Dow and Ashland Sign Ethyl Lactate Agreement: Green Solvents from Renewable Resources"; Business Wire; http//www.allbusiness.com/electronics/electronics-overview/5935032-1.html; Apr. 23, 2002; 3 pages.

International Search Report and Written Opinion for PCT/US10/21350; dated Mar. 3, 2010; 9 pages.

International Search Report and Written Opinion for PCT/US2010/060017, dated Aug. 25, 2011, 7 pages.

* cited by examiner

*Primary Examiner* — Joseph D Anthony

(74) *Attorney, Agent, or Firm* — Brown & Micheals, PC

(57) ABSTRACT

A terpene alcohol premix formulation raises the flash point of a volatile organic solvent to a level that results in a solvent solution that is less volatile. The catalytic formulation consists of a blend of two or more terpene alcohols and acetone. The blended terpene alcohols are present in the catalytic formulation in an amount of from about 5% to about 40%, by weight, based on the total weight of the terpene alcohol premix formulation. The remainder of the terpene alcohol premix formulation consists of from about 60% to about 95% acetone, by weight, based on the total weight of the terpene alcohol premix formulation.

19 Claims, No Drawings

US 8,092,715 B2

FORMULATIONS AND METHOD FOR RAISING THE FLASH POINTS OF VOLATILE ORGANIC SOLVENTS

FIELD OF THE INVENTION

The invention pertains to the field of organic solvents. More particularly, the invention pertains to formulations and methods for raising the flash points of various volatile organic solvents to improve the acceptance of and expand the potential uses for these solvents.

BACKGROUND OF THE INVENTION

All solvents are classified as Volatile Organic Compounds due to their photo-reactive qualities and Hazardous Air Pollutant (HAPS) status. The United States Environmental Protection Agency ("EPA") defines volatile organic compounds ("VOC's") or "Exempt VOC's" in the Federal Register under 40 CFR 51.100(s). They are further sub-classified based upon their vapor pressures, boiling points, and flash points. The flash point is critical because it is the point at which the liquid becomes a volatile vapor, mixes with oxygen, and thereby acquires its most combustible or flammable state. In the United States, the Environmental Protection Agency (EPA) and the Department of Transportation (DOT) have classified such compounds based on their volatilities or "flash points". The EPA and DOT Volatile Organic Compound ("VOC") classifications are as follows:

| | |
|---|---|
| Class I liquids (flammable) | flash point at or below 100° F. |
| Class II liquids (combustible) | flash point from 100° F. to below 140° F. |
| Class III liquids (combustible) | flash point above 140° F. to below 200° F. |

Obviously, the more flammable a solvent, the more restrictions exist on its use. The Federal Government has classified such solvents as Hazardous Materials or "HAZMATS". Further, manufacturers that utilize solvents must handle, store, warehouse, and ship the more volatile liquids more carefully and have to address issues involving atmospheric volatility, shelf life, and worker health concerns from prolonged exposure to these chemicals. If these solvents can be modified so that their flash points can be raised, this would result in significantly greater safety with respect to the handling, storing and shipping of these compounds as well as increasing their shelf lives. It is desirable therefore to raise the flash points of a variety of organic solvents without changing the solvent's strength and utility or substantially increasing its cost. This would expand the range of potential uses for these solvents.

Some terpene alcohols have the chemical formula: $C_{10}H_{18}O$. Terpenoid is the general name given to this class of compounds which are characterized by a repeating carbon skeleton of isoprene. Terpenoids are derived from plants, trees, flowers, and other vegetation which allows their classification as "green compounds". They come in the form of liquids, solids, waxes, oils, and alcohols. Terpenoids are divided into groups determined by the number of carbon atoms and repeating isoprene units. They may be formulated into acyclic, monocyclic, or polycyclic structures.

Terpene alcohols in various forms have been used for centuries in fragrances due to their signature odor and compatibility with other compounds and their minimal negative environmental impact. The flavor and fragrance industries divide terpineols, a type of terpene alcohol, into Alpha-, Beta- or Gamma-Terpineol, with Beta-Terpineol being non-naturally occurring. Terpene alcohols have been used for other purposes, such as disinfectants, cleaning compounds, soaps, cosmetics and colognes. They are also known to add, enhance or mask the odor of products which perhaps might be offensive to humans or animals.

U.S. Pat. No. 7,273,839 B2 discloses the use of an Alpha terpineol with petroleum based organic solvents and blends of solvents to increase the flash points of these solvents. The patent discloses that the addition of at least 10%, by weight, of a single Alpha terpineol to a solvent or combination of solvents increases the flash point of the blended compound. They show that at least 5% of one Alpha terpineol increases the flash points of specific solvents to provide increased options for which these solvents may be used. In one example, they claim that by adding 18 wt % of Alpha terpineol to acetone, they increased the solvent's flash point from 0° F. to 143.6° F. However, high Alpha terpineol loadings, such as in the 10-18%, by weight, range, often may cause rapid settling incompatibility and decreased shelf life, which substantially adds to the cost of formulating and using the solvent or combination of solvents.

SUMMARY OF THE INVENTION

Terpene alcohol premix formulations (TPFs) raise the flash points of organic solvents to a level that renders the resulting blended solvent solution less volatile. The premix formulations consist of a blend of two or more terpene alcohols and acetone. The blended terpene alcohols are present in the terpene alcohol premix formulation in an amount of from about 5% to about 40%, by weight, based on the total weight of the terpene alcohol premix formulation. The remainder of the terpene alcohol premix formulation consists of from about 60% to about 95% acetone, by weight, based on the total weight of the terpene alcohol premix formulation.

When the terpene alcohol premix formulation is blended with a volatile organic compound ("VOC"), having a low virgin flash point, the resulting blended solvent solution possesses a significantly higher flash point. By raising the flash point of a low VOC or Exempt VOC, its safety status and overall utility is improved for a variety of industrial and commercial uses. Since the terpene alcohol premix formulation is based upon an Exempt VOC (acetone), it may be used to reduce the total VOC emissions of standard solvents or maintain the Exempt VOC status of Exempt VOC solvents. Four of the Exempt VOC's tested hereinbelow have flash points below 80° F., thus limiting their use because of safety concerns. In the tested solvents, the terpene alcohol premix formulation elevates these solvents' flash points to at least 140° F. without altering their individual Exempt VOC status. In addition, with the shelf life of the original low VOC solvent being improved, the scope of potential uses to which the blended solvent solution may be applied is significantly increased.

DETAILED DESCRIPTION OF THE INVENTION

The formulations increase the flash points of low flash point compounds, such as organic solvents known as VOC's (Volatile Organic Compounds), to levels that permit an expanded range of uses for such compounds. In addition, the formulation of the invention improves the storage life (or, "shelf life") of these VOC's.

For purposes of this disclosure, the formulation is referred to hereinafter as a "terpene alcohol premix formulation" or "TPF". It consists of a 1:1, by weight, blend of two terpene alcohols, added to acetone. The blended terpene alcohol/acetone composition is the terpene alcohol premix formulation. The amount, by weight, of the 1:1 blend of terpene alcohols in the terpene alcohol premix formulation is from about 5% to about 40%. Preferably, the amount is from about 7% to about 20%, by weight, based on the total weight of the terpene alcohol premix formulation. Most preferably, the amount of the 1:1 blend of terpene alcohols is approximately 15%, by weight, based on the total weight of the terpene alcohol premix formulation.

The amount of acetone, by weight, based on the total weight of the terpene alcohol premix formulation, is from about 60% to about 95%. Preferably, the amount of acetone is from about 80% to about 90%, by weight, based on the total weight of the terpene alcohol premix formulation. Most preferably, the amount of acetone in the terpene alcohol premix formulation is about 85%, by weight, based on the total weight of the terpene alcohol premix formulation.

Examples of terpene alcohols include geraniol, citronellol, nerol, menthol, nerolidol, and farnesol. These terpene alcohols have a vapor pressure that is less than 0.05 mm Hg, thus complying with Exempt VOC standards. These compounds can be acquired from manufacturers such as International Flavors and Fragrances, Inc. ("IFF") and Millennium Chemicals, Inc ("MIL"). "A-JAX" is an alpha-Terpineol available from IFF, having the chemical formula: C10-H18-O. Mil-350 is a Terpineol available from MIL having the chemical structure 4-trimethyl 3-cyclohexene-1-methanol.

The amount of the terpene alcohol premix formulation added to the volatile organic compound is from about 20 to about 30%, by weight, based on the total weight of the terpene alcohol premix formulation and the volatile organic compound solution. Preferably, the amount of the terpene alcohol premix formulation is about 23%, by weight, based on the total weight of the terpene alcohol premix formulation and the volatile organic compound solution. The amount of the terpene alcohol component in the final solution is approximately 3%, by weight, based on the weight of the terpene alcohol premix formulation and the volatile organic compound solution.

EXAMPLE I

Increasing VOC Flash Points

A number of Volatile Organic Compounds having low virgin flash points were tested by blending them with the terpene alcohol premix formulation (TPF) described hereinabove. The volatile organic compounds shown below are merely exemplary and are not meant to be limiting in scope. The terpene alcohol premix formulation may be blended with any other volatile organic compound to achieve essentially the same results as exemplified below.

1) Acetone Virgin Flash Point: −4° F.

To 77 grams of acetone were added 23 grams of the terpene alcohol premix formulation ("TPF"). The TPF was formulated with 3 grams (15%, by weight, based on the total weight of the TPF) of a 1:1, by weight, blend of Alpha-350:Alpha-Jax, added to 20 grams (85%, by weight, based on the total weight of the TPF) of acetone. The total weight of the 1:1 Alpha terpineol component was 3%, based upon the total weight of the blended TPF/acetone solution. The blended solution was mixed well and allowed to sit for @24 hours at ambient temperature.

The blended solution exhibited a flash point of 143° F.

2) Methyl Acetate Virgin Flash Point: 15° F.

To 77 grams of methyl acetate were added 23 grams of the TPF blend set forth above in example 1. As above, the total weight of the 1:1 Alpha terpineol component was 3%, based upon the total weight of the blended TPF/methyl acetate solution.

The blended solution exhibited a flash point of 140° F. Comparison test: To further show the benefits provided by the TPF, an additional test was conducted where the acetone was omitted. Only 3%, by weight, based on the total weight of the blended solution, was added to 97%, by weight, of methyl acetate. In this case, the flash point was only increased to 115° F. This shows that the combination of a blend of two Alpha terpineols and acetone produces a marked increase in the flash point of this VOC.

3) P-chlorobenzotrifluoride Virgin Flash Point: 109° F.

To 77 grams of P-chlorobenzotrifluoride were added 23 grams of the TPF blend set forth in example 1. As above, the total weight of the 1:1 Alpha terpineol component was 3%, based upon the total weight of the blended TPF/P-chlorobenzotrifluoride solution.

The blended solution exhibited a flash point of 175° F. Comparison test: As above, the acetone was omitted from a further test. Only 3%, by weight, based on the total weight of the blended solution, was added to 97%, by weight, of P-chlorobenzotrifluoride. The resulting flash point had only increased to 125° F.

4) Tertiary Butyl Acetate Virgin Flash Point: 40° F.

To 77 grams of tertiary butyl acetate were added 23 grams of the TPF blend set forth in example 1. As above, the total weight of the 1:1 Alpha terpineol component was 3%, based upon the total weight of the blended TPF/tertiary butyl acetate solution.

The blended solution exhibited a flash point of 142° F. Comparison test: As above, the acetone was omitted from a further test. Only 3%, by weight, based on the total weight of the blended solution, was added to 97%, by weight, of tertiary butyl acetate. The resulting flash point had only increased to 122° F.

5) Dimethyl Carbonate Virgin Flash Point: 63° F.

To 77 grams of dimethyl carbonate were added 23 grams of the TPF blend set forth in example 1. As above, the total weight of the 1:1 Alpha terpineol component was 3%, based upon the total weight of the blended TPF/dimethyl carbonate solution.

The blended solution exhibited a flash point of 170° F. Comparison test: As above, the acetone was omitted from a further test. Only 3%, by weight, based on the total weight of the blended solution, was added to 97%, by weight, of dimethyl carbonate. The resulting flash point remained unchanged.

It is readily apparent from the above comparison testing that the blending of Alpha terpineols with acetone, the latter of which has a very low virgin flash point, results in a significant increase in the flash point of the Terpineol catalytic formulation, rather than a decrease, as might have been expected.

Hansen Solubility Parameters

A solubility standard has been developed which is referred to as the Hanson Solubility Parameters. These parameters identify and quantify the ability of solvents to dissolve other materials and form stable solutions. Solvents (VOC's and Exempt VOC's) having solubility parameter values ranging from approx. 8.0 to 10.0 are generally considered to be good solvents to dissolve a wide selection of coating resins and polymers. The following Hansen Solubility Parameter values are calculated based upon virgin solvent values compared with the respective solvent/TPF blended solution. The resulting comparison of the above identified solvents indicates a positive shift in the Hansen Solubility Parameter values, with the objective of obtaining or maintaining a Hanson value of from 8.0 to 10.0.

Hansen Solubility Parameter Evaluation:

| Solvent (Exempt VOC) | Hansen Value | Solvent/TPF Value |
|---|---|---|
| 1. Acetone | 9.8 | 9.8 (same) |
| 2. Methyl Acetate | 9.5 | 9.58 |
| 3. P-Chlorobenzotrifluoride | 8.63 | 8.92 |
| 4. Tert-Butyl Acetate | 8.5 | 8.83 |
| 5. Dimethyl Carbonate | 9.7 | 9.73 |

EXAMPLE II

Varying Amount of Acetone in TPF

A

Comparison testing was conducted to determine the optimum amount of acetone in the TPF for a specific VOC. The same VOC's as identified above in Example I were employed.

1) Methyl Acetate was selected for the first test. Using the standard TPF, the flash point was determined to be 140° F. Adjusting the acetone level to 90%, 92% and 94%, by weight, based on the total weight of the TPF, the flash point was elevated to a peak of 145° F. at 90%. A sharp drop off in the efficiency of the TPF was noticed when the amount of acetone was reduced to 77% and 83%, respectively, by weight.

2) Using the standard TPF, the flash point of P-Chlorobenzotrifluoride was determined to be 175° F. Adjusting the acetone level to 90%, 92% and 94%, by weight, based on the total weight of the TPF, the flash point was elevated to a peak above 180° F. at 92% acetone. A sharp drop off in the efficiency of the TPF was noticed when the amount of acetone was reduced to 86%, by weight.

3) Using the standard TPF, the flash point of Tertiary Butyl Acetate was determined to be 142° F. Adjusting the acetone level to 90%, 92% and 94%, by weight, based on the total weight of the TPF, the flash point was elevated to a peak above 146° F. at 90% acetone. A sharp drop off in the efficiency of the TPF was noticed when the amount of acetone was reduced to 77%, by weight.

4) Using the standard TPF, the flash point of Dimethyl Carbonate was determined to be 170° F. Adjusting the acetone level to 90%, 92% and 94%, by weight, based on the total weight of the TPF, the flash point was elevated to a peak above 178° F. at 90% acetone. A sharp drop off in the efficiency of the TPF was noticed when the amount of acetone was reduced to 77%, by weight.

These test results indicate that there is an effective peak ratio between acetone and Terpineol components at an acetone loading of 86-92%, by weight, and an Alpha terpineol loading of approximately 8-14%, by weight, based on the total weight of the TPF.

B

By varying the relative amounts of acetone in a specific terpene alcohol premix formulations, one can fine tune the physical properties of a VOC blended with such TPF solution. The following examples show that different amounts of acetone in the TPF may be required to provide optimum physical performance levels of the blended TPF/VOC solution.

The improved physical characteristics include (a) increased flash point; (b) reduced HAP emissions; (c) improved water miscibility, and (d) improved solvent strength, as defined by the synergistic compounding of the TPF and specific VOC's. Acetone enhances solvency. Solvency is referred to as "blend efficiency" of the solvent compound(s) and is quantified by a solvent's Hansen Solubility Parameter value. The TPF enables "blend efficiency" without violating air pollution regulations because the TPF itself is an Exempt VOC.

1) Xylene Virgin Flash Point: 80° F.

67%, by weight, of xylene was added to 33%, by weight, based on the total weight of the xylene/TPF blended solution. The amount of the 1:1 Alpha terpineol component, by weight, based on the total weight of the VOC/TPF solution, remains constant at 3%. The amount of acetone in this blend was 30%, by weight, based on the total weight of the xylene/TPF solution.

The blended solution exhibited a flash point of 160° F.

2) Methanol Virgin Flash Point: 54° F.

70%, by weight, of methanol was added to 30%, by weight, based on the total weight of the methanol/TPF blended solution. With the amount of the Alpha terpineol component remaining constant at 3%, the acetone component was 27%, by weight, based on the total weight of the VOC/TPF solution.

The blended solution exhibited a flash point of 145° F.

3) Isopropyl Alcohol Virgin Flash Point: 63° F.

70%, by weight, of isopropyl alcohol was added to 30%, by weight, based on the total weight of the isopropyl alcohol/TPF blended solution. With the amount of the Alpha terpineol component remaining constant at 3%, the acetone component was 27%, by weight, based on the total weight of the VOC/TPF solution.

The blended solution exhibited a flash point of 155° F.

4) Methyl Ethyl Ketone Virgin Flash Point: 25° F.

70%, by weight, of methyl ethyl ketone was added to 30%, by weight, based on the total weight of the methyl ethyl ketone/TPF blended solution. With the amount of the Alpha terpineol component remaining constant at 3%, the acetone component was 27%, by weight, based on the total weight of the VOC/TPF solution.

The blended solution exhibited a flash point of 160° F.

5) Mineral Spirits Virgin Flash Point: 110° F.

70%, by weight, of Mineral Spirits was added to 30% by weight, based upon the total weight of the Mineral Spirits/TPF blended solution. With the amount of the Alpha Terpineol component remaining constant at 3%, the acetone component was 27%, by weight, based upon the total weight of the VOC/TPF solution.

The blended solution exhibited a flash point of 150° F.

Hansen Solubility Parameters

The following Hansen Solubility Parameter values were calculated based upon virgin solubility values of the foregoing solvents compared with their respective solvent/TPF blended solution. The resulting value comparisons of the above identified solvents indicates a positive shift toward improving solvency, with the objective of approaching or maintaining a Hanson Solubility Parameter value of from 8.0 to 10.0.

Hansen Solubility Parameter Evaluation:

| Solvent (VOC) | Hansen Value | Solvent/TPF Value |
|---|---|---|
| 1. Xylene | 8.7 | 8.98 |
| 2. Methanol | 14.6 | 13.40 |
| 3. Isopropyl Alcohol | 11.5 | 11.08 |
| 4. Methyl Ethyl Ketone | 9.3 | 9.43 |
| 5. Mineral Spirits | 7.7 | 8.23 |

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for raising the flash point of a volatile organic compound comprising:
    combining a formulation consisting essentially of a blend of at least two terpene alcohols and acetone with the volatile organic compound to create a solution consisting essentially of the formulation and the volatile organic compound;
    wherein the blend is present in an amount in a range of about 5 to about 40 wt % based on the total weight of the formulation; and
    wherein the flash point of the solution is greater than the flash point of the volatile organic compound.

2. The method of claim 1 wherein the amount of the formulation added to the volatile organic compound is in a range of about 20 to about 30 wt % based on the total weight of the formulation and the volatile organic compound.

3. The method of claim 1, wherein the amount of the blend is about 3 wt % based on the total weight of the formulation and the volatile organic compound.

4. The method of claim 1, wherein the addition of the formulation increases the Hansen Solubility Parameter value of the volatile organic compound.

5. The method of claim 1 further comprising combining the blend and the acetone to form the formulation.

6. The method of claim 1, wherein the blend is present in an amount in a range of about 7 to about 20 wt % based on the total weight of the formulation.

7. The method of claim 6, wherein the amount of the formulation added to the volatile organic compound is in a range of about 20 to about 30 wt % based on the total weight of the formulation and the volatile organic compound, the volatile organic compound has a flash point of 110° F. or less, and the formulation raises the flash point to at least 140° F.

8. The method of claim 6, wherein the amount of the formulation added to the volatile organic compound is in a range of about 20 to about 30 wt % based on the total weight of the formulation and the volatile organic compound and the formulation raises the flash point of the volatile organic compound by at least 40° F.

9. The method of claim 1, wherein the volatile organic compound has a flash point of 110° F. or less and the formulation raises the flash point to at least 140° F.

10. The method of claim 1, wherein the formulation raises the flash point of the volatile organic compound by at least 40° F.

11. A solution consisting essentially of:
    a formulation consisting essentially of:
        (a) a blend of at least two terpene alcohols; and
        (b) acetone;
        wherein the blend is present in an amount in a range of about 5 to about 40 wt % based on the total weight of the formulation; and
    a volatile organic compound;
    wherein the flash point of the solution is greater than the flash point of the volatile organic compound.

12. The solution of claim 11, wherein the blend consists essentially of a 1:1 ratio, by weight, of a first terpene alcohol and a second terpene alcohol.

13. The solution of claim 11, wherein the blend is present in an amount in a range of about 7 to about 20 wt % based on the total weight of the formulation.

14. The solution of claim 13, wherein the formulation is present in an amount in a range of about 20 to about 30 wt % based on the total weight of the solution, the volatile organic compound has a flash point of 110° F. or less, and the solution has a flash point of at least 140° F.

15. The solution of claim 13, wherein the formulation is present in an amount in a range of about 20 to about 30 wt % based on the total weight of the solution and the flash point of the solution is greater than the flash point of the volatile organic compound by at least 40° F.

16. The solution of claim 11, wherein the formulation is present in an amount in a range of about 20 to about 30 wt % based on the total weight of the solution.

17. The solution of claim 11, wherein the volatile organic compound is selected from the group consisting of:
    a) methyl acetate;
    b) p-chlorobenzotrifluoride;
    c) tertiary butyl acetate;
    d) dimethyl carbonate;
    e) xylene;
    f) methanol;
    g) isopropyl alcohol;
    h) methyl ethyl ketone; and
    i) mineral spirits.

18. The solution of claim 11, wherein the volatile organic compound has a flash point of 110° F. or less and the solution has a flash point of at least 140° F.

19. The solution of claim 11, wherein the flash point of the solution is greater than the flash point of the volatile organic compound by at least 40° F.

* * * * *